(12) United States Patent
Huthmacher et al.

(10) Patent No.: US 10,857,295 B2
(45) Date of Patent: Dec. 8, 2020

(54) MEDICAMENT DELIVERY DEVICE (71) Applicant: Sanofi-Aventis Deutschland GMBH, Frankfurt am Main (DE)

(72) Inventors: Winfried Huthmacher, Frankfurt am Main (DE); Peter Nober, Rommersheim (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 12 days.

(21) Appl. No.: 15/031,632

(22) PCT Filed: Oct. 21, 2014

(86) PCT No.: PCT/EP2014/072557
§ 371 (c)(1),
(2) Date: Apr. 22, 2016

(87) PCT Pub. No.: WO2015/062915
PCT Pub. Date: May 7, 2015

(65) Prior Publication Data
US 2016/0263325 A1    Sep. 15, 2016

(30) Foreign Application Priority Data
Oct. 31, 2013   (EP) .................................... 13191199

(51) Int. Cl.
*A61M 5/20*    (2006.01)
*A61M 5/32*    (2006.01)
(Continued)

(52) U.S. Cl.
CPC ........ *A61M 5/2033* (2013.01); *A61M 5/3202* (2013.01); *A61M 5/3243* (2013.01);
(Continued)

(58) Field of Classification Search
CPC .... A61M 2005/202; A61M 2005/2485; A61M 2005/3125; A61M 2005/3247;
(Continued)

(56) References Cited

U.S. PATENT DOCUMENTS 5,271,744 A   12/1993  Kramer et al.
5,478,316 A   12/1995  Bitdinger et al.
(Continued)

FOREIGN PATENT DOCUMENTS

EP    2399628    12/2011
EP    2468338     6/2012
(Continued)

OTHER PUBLICATIONS

International Preliminary Report on Patentability in International Application No. PCT/EP2014/072557, dated May 3, 2016, 9 pages.
(Continued)

*Primary Examiner* — Quynh-Nhu H. Vu
(74) *Attorney, Agent, or Firm* — Fish & Richardson P.C.

(57) ABSTRACT

Described is a medicament delivery device (1) comprising a body (2), a container carrier (7) slidably disposed in the body (2), and a sleeve (6) slidably coupled to the container carrier (7).

16 Claims, 9 Drawing Sheets

(51) Int. Cl.
  *A61M 5/31* (2006.01)
  *A61M 5/315* (2006.01)
  *A61M 5/24* (2006.01)
  *A61M 5/46* (2006.01)

(52) U.S. Cl.
  CPC ....... *A61M 5/31505* (2013.01); *A61M 5/3213* (2013.01); *A61M 5/46* (2013.01); *A61M 2005/202* (2013.01); *A61M 2005/2485* (2013.01); *A61M 2005/3125* (2013.01); *A61M 2005/3247* (2013.01); *A61M 2005/3267* (2013.01); *A61M 2205/58* (2013.01)

(58) Field of Classification Search
  CPC ...... A61M 2005/3267; A61M 2205/58; A61M 5/2033; A61M 5/31505; A61M 5/3202; A61M 5/3213; A61M 5/3243; A61M 5/04
  See application file for complete search history.

(56) References Cited

U.S. PATENT DOCUMENTS

| | | | |
|---|---|---|---|
| 5,658,259 | A | 8/1997 | Pearson et al. |
| 6,001,082 | A * | 12/1999 | Dair .................. A61M 5/31525 604/187 |
| 6,258,068 | B1 | 7/2001 | Kirchhofer et al. |
| 7,357,790 | B2 | 4/2008 | Hommann et al. |
| 7,695,453 | B2 * | 4/2010 | Marshall ............. A61M 5/2033 604/110 |
| 8,016,797 | B2 | 9/2011 | Gratwohl et al. |
| 8,945,049 | B2 | 2/2015 | Hommann et al. |
| 2011/0092915 | A1 * | 4/2011 | Olson ................. A61M 5/3202 604/198 |
| 2011/0172602 | A1 * | 7/2011 | Eaton .................. A61M 5/2033 604/134 |
| 2012/0089098 | A1 * | 4/2012 | Boyd ..................... A61M 5/24 604/189 |
| 2012/0289905 | A1 * | 11/2012 | Julian ..................... A61M 5/20 604/189 |
| 2013/0310746 | A1 * | 11/2013 | Wozencroft ........ A61M 5/2033 604/131 |

FOREIGN PATENT DOCUMENTS

| | | |
|---|---|---|
| GB | 2463071 | 3/2010 |
| JP | 2013-529520 | 7/2013 |
| WO | WO2005/070481 | 8/2005 |
| WO | WO2011/047298 | 4/2011 |
| WO | WO 2012/000872 | 1/2012 |
| WO | WO 2012/067584 | 5/2012 |
| WO | WO2012/093070 | 7/2012 |
| WO | WO 2012/093072 | 7/2012 |
| WO | WO2012/103141 | 8/2012 |

OTHER PUBLICATIONS

International Search Report and Written Opinion in International Application No. PCT/EP2014/072557, dated Feb. 2, 2015, 13 pages.

Rote Liste, "50. Hypophysen-, Hypothalamushormone, andere regulatorische Peptide u. ihre Hemmstoffe," Chapter 50, ed. 2008, 20 pages.

* cited by examiner

MEDICAMENT DELIVERY DEVICE

CROSS-REFERENCE TO RELATED APPLICATIONS

This application is a U.S. national stage application under 35 USC § 371 of International Application No. PCT/EP2014/072557, filed on Oct. 21, 2014, which claims priority to European Patent Application No. 13191199.2, filed on Oct. 31, 2013, the entire contents of which are incorporated herein by reference.

TECHNICAL FIELD

The invention relates to a medicament delivery device.

BACKGROUND OF THE INVENTION

Administering an injection is a process which presents a number of risks and challenges for users and healthcare professionals, both mental and physical. Pre-filled syringes that are filled with a selected dosage of a medicament for administering the medicament to a patient are known in the art. Conventional medicament delivery devices comprising a needle safety system for preventing needle stick injuries are also known.

There remains a need for an improved medicament delivery device.

SUMMARY OF THE INVENTION

In an exemplary embodiment, a medicament delivery device according to the present invention comprises a body, a container carrier slidably disposed in the body, and a sleeve slidably coupled to the container carrier. The container carrier includes at least one first leg having a first protrusion and a second protrusion proximal of the first protrusion. The sleeve includes a collar adapted to abut the first protrusion and the second protrusion.

In an exemplary embodiment, the container carrier includes at least one second leg biased radially outward. The body includes at least one axial stop adapted to axially abut the at least one second leg.

In an exemplary embodiment, the container carrier includes at least one third leg biased radially outward. The sleeve includes at least one sleeve leg adapted to radially abut the at least one third leg when the sleeve is in a retracted position relative to the body. The at least one third leg is adapted to axially abut the at least one sleeve leg to lock the sleeve is in an extended position relative to the body.

In an exemplary embodiment, the at least one first leg, the at least one second leg and the at least one third leg are coupled to a periphery of a proximal portion of the container carrier, and the at least one first leg, the at least one second leg and the at least one third leg extend in a distal direction from the proximal portion.

In an exemplary embodiment, the medicament delivery device further comprises a plunger rod disposed within the body. The plunger rod is fixed to the body.

In an exemplary embodiment, the medicament delivery device further comprises a sleeve spring biasing the sleeve relative to the container carrier. The sleeve spring biases the sleeve toward the first protrusion.

In an exemplary embodiment, the medicament delivery device further comprises a container spring biasing the carrier relative to the body.

In an exemplary embodiment, the sleeve includes one or more sleeve windows.

In an exemplary embodiment, the medicament delivery device further comprises a cap removably coupled to the body. The cap includes a viewing window. The cap includes one or more indicia indicating an intended orientation of the device.

In an exemplary embodiment, the medicament delivery device further comprises a container including a medicament. The proximal portion of the container carrier is adapted to receive the container.

Further scope of applicability of the present invention will become apparent from the detailed description given hereinafter. However, it should be understood that the detailed description and specific examples, while indicating exemplary embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
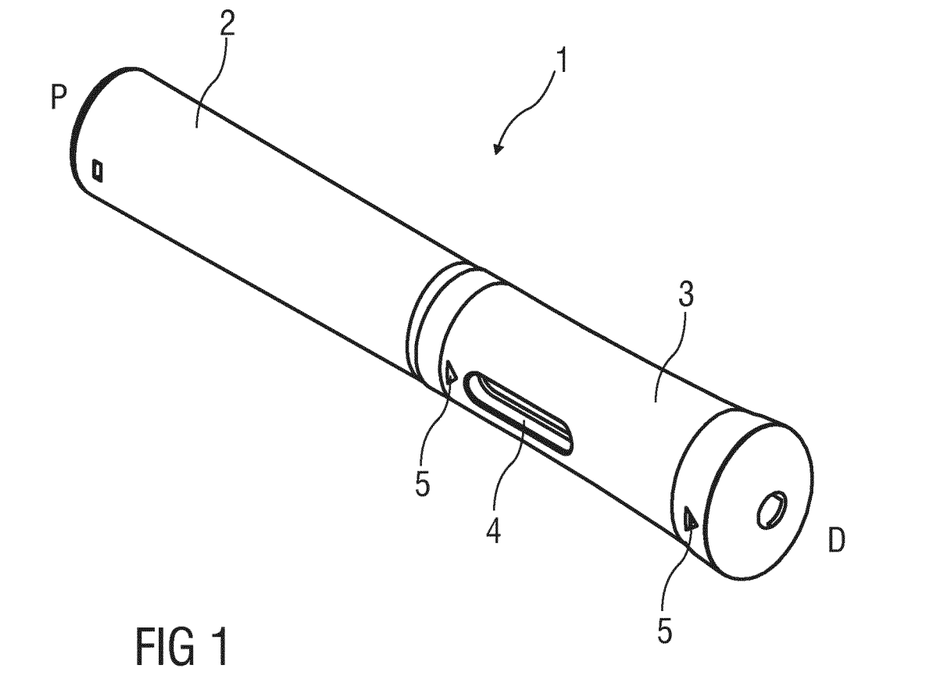
FIG. 1 is a schematic perspective view of an exemplary embodiment of a medicament delivery device prior to use.

FIG. 1 is a perspective view of an exemplary embodiment of a medicament delivery device 1 according to the present invention. The medicament delivery device 1 comprises a body 2 which may be generally cylindrical. In an exemplary embodiment, a cap 3 may be removably coupled to the body 2. The cap 3 may include a viewing window 4 (e.g., an opening or a substantially transparent piece of material). The cap 3 may further include one or more indicia 5 for providing a visual and/or tactile indication of use (e.g., which end of the device 1 should be applied to an injection site, etc.). For example, in an exemplary embodiment, the indicia 5 include one or more arrows (painted or embossed) pointing toward a distal end of the device 1.

Figure 2:
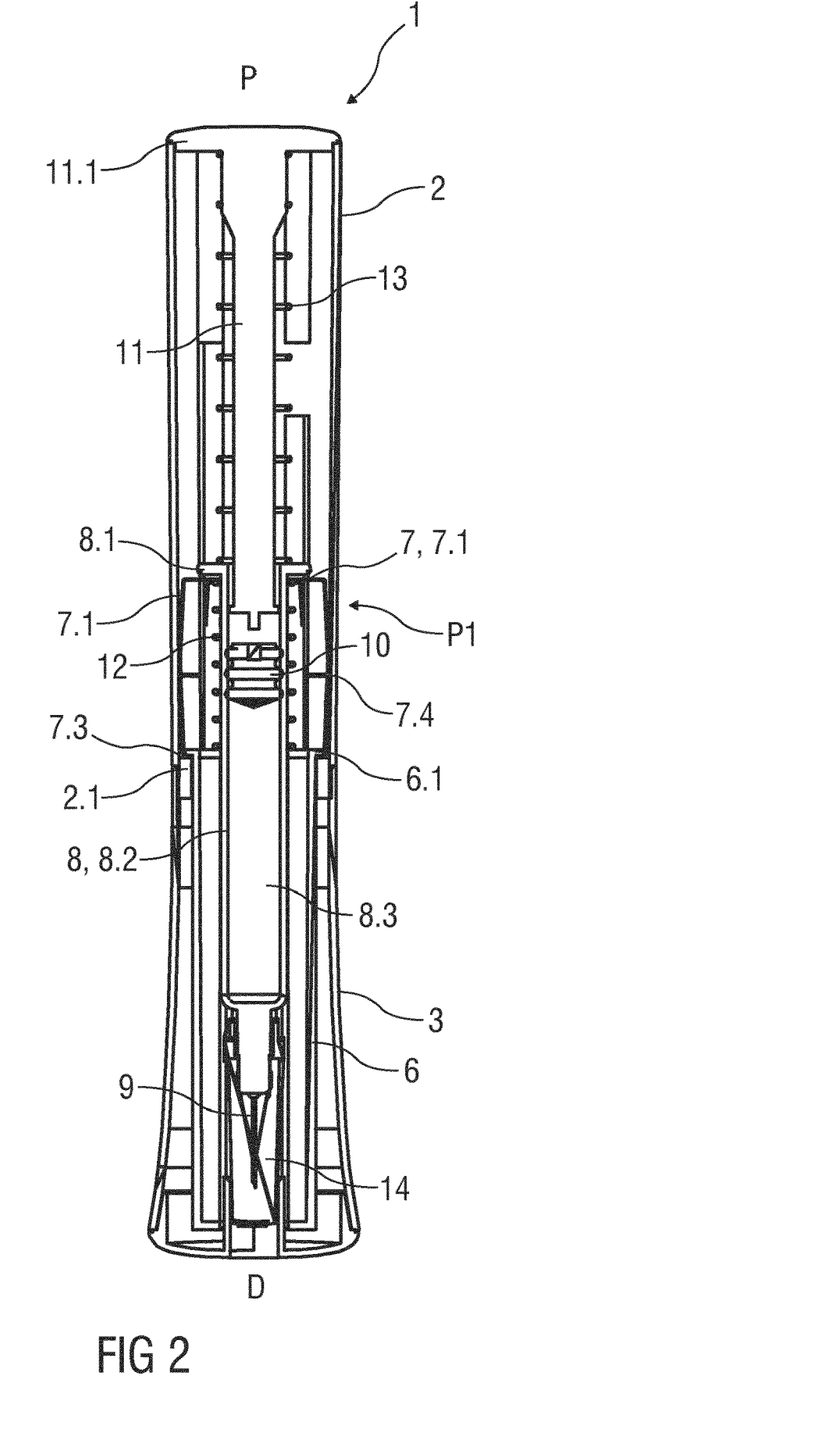
FIG. 2 is a schematic longitudinal section of an exemplary embodiment of a medicament delivery device prior to use.

FIG. 2 is a longitudinal section of an exemplary embodiment of a medicament delivery device 1 according to the present invention. A sleeve 6 is slidably coupled to the body 2. For example, the sleeve 6 may be telescoped within the body 2. In an exemplary embodiment, the sleeve 6 comprises one or more lateral sleeve windows 6.2 adapted to axially align with the viewing windows 4 (e.g., an opening or a substantially transparent piece of material) in the cap 3 when the sleeve 6 is in an extended position (as shown in FIG. 2) relative to the body 2.

In an exemplary embodiment, a container carrier 7 slidably disposed in the body 2. The container carrier 7 is adapted to retain a medicament container, e.g., a syringe 8, an ampoule, a cartridge, etc. For example, the syringe 8 includes a syringe barrel 8.2 arranged as a hollow cylinder defining a cavity 8.3 for receiving a medicament. A needle 9 is arranged at a distal end of the syringe barrel 8.2 in a manner to be in fluid communication with the cavity 8.3. A stopper 10 is disposed within the syringe barrel 8.2 for proximally limiting the cavity 8.3. The stopper 10 may be displaced within the syringe barrel 8.2 for ejecting the medicament from the cavity 8.3 through the needle 9.

Figure 3:
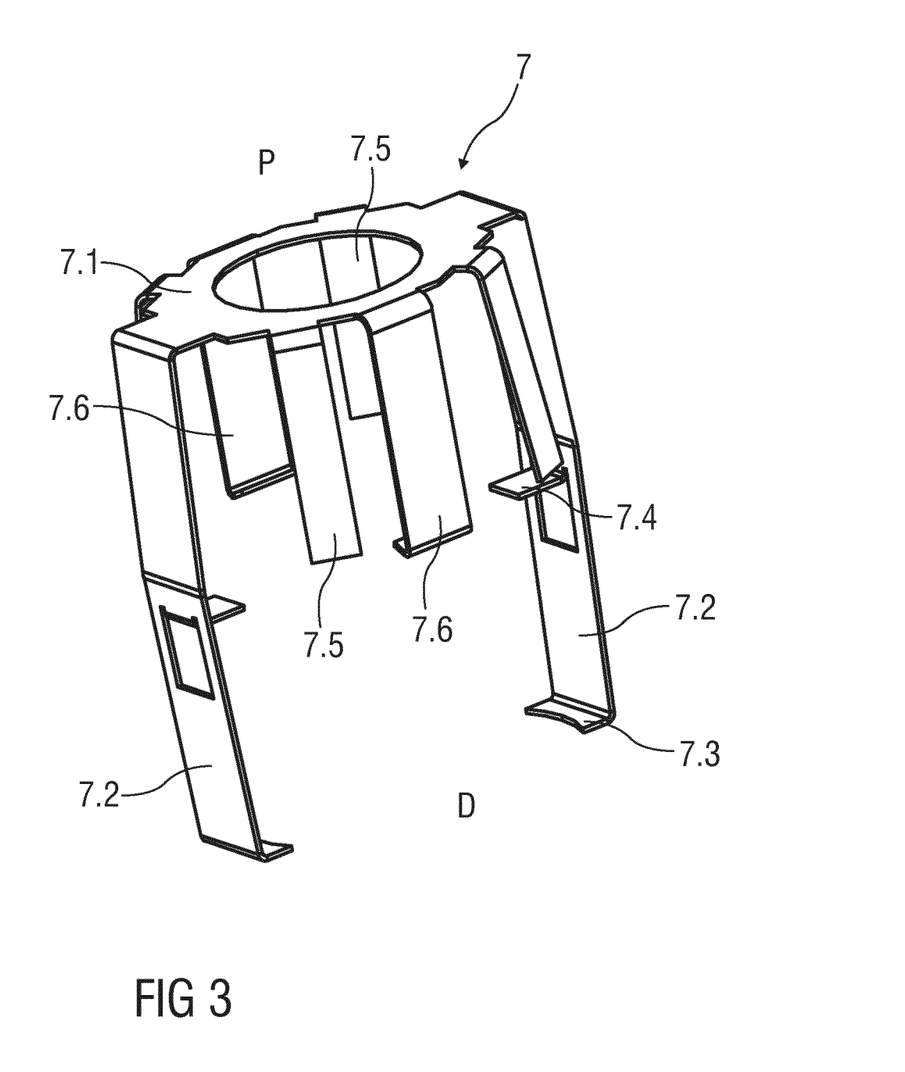
FIG. 3 is a schematic perspective view of an exemplary embodiment of a container carrier according to the present invention.

FIG. 3 shows an exemplary embodiment of a container carrier 7 according to the present invention. The container carrier 7 comprises a proximal portion 7.1 adapted to engage the medicament container. For example, the proximal portion 7.1 may support a flange 8.1 on a syringe barrel 8.2 of the syringe 8 such that the syringe 8 is prevented from moving in the distal direction D relative to the carrier 7. One or more first legs 7.2 extend distally from the proximal portion 7.1. In an exemplary embodiment, the first leg 7.2 comprises a radially inwardly directed first protrusion 7.3 arranged on a distal end of the first leg 7.2 and a radially inwardly directed second protrusion 7.4 proximal of the first protrusion 7.3. The first protrusion 7.3 and the second protrusion 7.4 are adapted to abut a collar 6.1 on the sleeve 6 for limiting axial movement of the sleeve 6 relative to the carrier 7. The first leg 7.2 is adapted to distally abut a first axial stop 2.1 in the body 2 limiting movement of the carrier 7 in the distal direction relative to the body 2.

One or more second legs 7.5 extend distally from the proximal portion 7.1. The second leg 7.5 is biased radially outward. The second leg 7.5 is adapted to engage one or more first ribs 2.2 (FIG. 5) in the body 2.

One or more third legs 7.6 extend distally from the proximal portion 7.1. The third leg 7.6 is biased radially outward. The third leg 7.5 is adapted to engage one or more second ribs 2.4 (FIG. 9) in the body 2.

In an exemplary embodiment, the sleeve 6 comprises one or more sleeve legs 6.3 extending in the proximal direction P beyond the collar 6.1. The sleeve legs 6.3 are adapted to radially outwardly support the third legs 7.6 of the carrier 7 such that they cannot deflect radially outwards depending on the axial position of the sleeve 6 relative to the carrier 7, as explained below with regard to FIG. 8.

Referring again to FIG. 2, a piston rod 11 is arranged within the body 2 in a manner to engage the stopper 10 for displacing it within the syringe barrel 8.2. In an exemplary embodiment, the piston rod 11 is attached to the body 2, preventing relative movement between the piston rod 11 and the body 2. In an exemplary embodiment the piston rod 11 may be integrally shaped with the body 2, or in another exemplary embodiment, the piston rod 11 may be secured to the body 2 by latches 11.2 (shown in FIG. 4). In an exemplary embodiment, prior to use, an axial gap may be present between a distal end of the piston rod 11 and a proximal end of the stopper 10. The axial gap may prevent force being applied to the stopper 10 prior to use.

In an exemplary embodiment, a sleeve spring 12 is arranged between the carrier 7 and the sleeve 6 in a manner biasing the sleeve 6 in the distal direction D relative to the carrier 7 such that the collar 6.1 of the sleeve 6 abuts the first protrusion 7.3 of the carrier 7.

In an exemplary embodiment, a container spring 13 is arranged over the piston rod 11 between a proximal end face 11.1 of the piston rod 11 and the proximal flange 8.1 of the syringe 8 thus biasing the syringe 8 in the distal direction D relative to the piston rod 11 and body 2.

In an exemplary embodiment, a protective needle shield 14 is arranged over the needle 9. The cap 3 is adapted to engage (e.g., by a barb, hook, latch, etc.) the needle shield 14 in manner to remove it from the needle 9 once the cap 3 is removed from the body 2 by pulling it in the distal direction D. A snap feature 2.6 may be arranged on the body 2 for snap fitting the cap 3 to the body 2.

In order to perform an injection, the medicament delivery device 1 may be operated according to the following exemplary steps.

The cap 3 is pulled in the distal direction D relative to the body 2 thereby also pulling the protective needle shield 14 off the needle 9. The syringe 8 is prevented from moving in the distal direction D as its proximal flange 8.1 abuts the proximal portion 7.1 of the carrier 7, and the carrier 7 is prevented from moving in the distal direction D as the first leg 7.1 of the carrier 7 distally abuts a first axial stop 2.1 in the body 2. The collar 6.1 on the sleeve 6 distally abuts the first protrusion 7.3 on the first leg 7.2 such that the sleeve 6 is also prevented from moving in the distal direction D.

Figure 4:
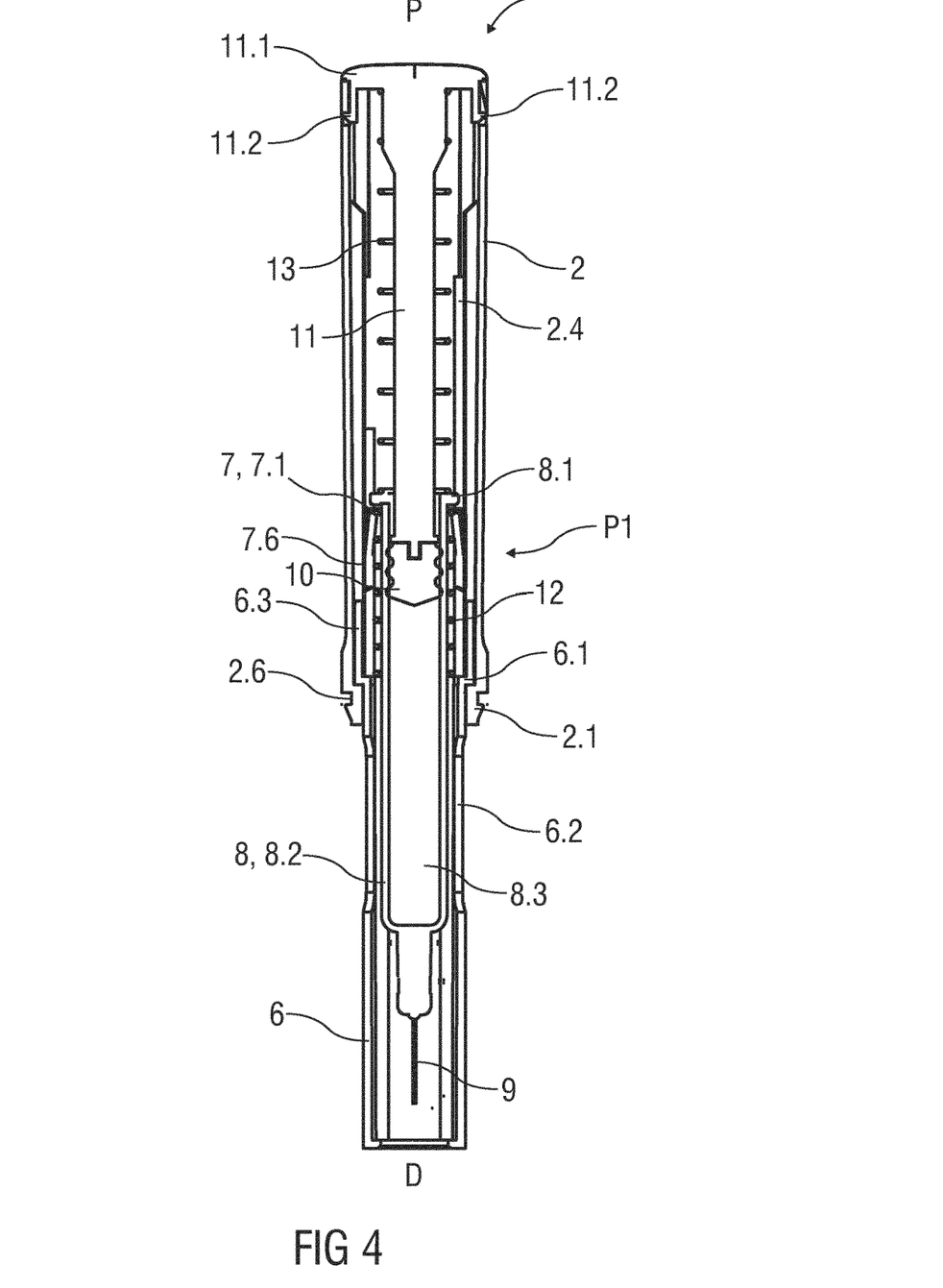
FIG. 4 is a schematic longitudinal section of an exemplary embodiment of a medicament delivery device prior to use.

FIG. 4 is a schematic longitudinal section of an exemplary embodiment of a medicament delivery device 1 according to the present invention prior to use. The needle 9 is located within the sleeve 6 preventing a user from touching and seeing it. In this state the medicament delivery device 1 may be held at the body 2 and the sleeve 6 may be pushed against an injection site, e.g. a patient's skin. Consequently the sleeve 6 moves in the proximal direction P relative to the body 2 against the force of both the sleeve spring 12 and the container spring 13. The sleeve spring 12 and the container spring 13 are selected such that a spring force of the sleeve spring 12 is less than a spring force of the container spring 13. Due to the movement of the sleeve 6 in the proximal direction P, the sleeve spring 12 will be compressed as the collar 6.1 of the sleeve 6 disengages the first protrusion 7.3 and moves towards the second protrusion 7.4, allowing the sleeve 6 to retract into the body 2. The carrier 7 and the syringe 8 remain in position (abutting the first axial stop 2.1) due to the force of the container spring 13. As the syringe 8 and the needle 9 stay in position relative to the body 2 while the sleeve 6 moves in the proximal direction P, a distal tip of the needle 9 is exposed beyond a distal end of the sleeve 6 and inserted into the injection site. Once the collar 6.1 abuts the second protrusion 7.4, movement of the sleeve 6 in the proximal direction P relative to the carrier 7 stops. The needle 9 has reached its insertion depth. Any further movement of the sleeve 6 relative to the body 2 in the proximal direction P causes the carrier 7 with the syringe 8 to move proximally relative to the body 2, because the collar 6.1 pushes the second protrusion 7.4. This proximal movement thus compresses the container spring 13. As the piston rod 11 is coupled to the body 2, this proximal movement causes the piston rod 11 to abut the stopper 10 and displace it within the syringe barrel 8.2 ejecting the medicament from the cavity 8.3 through the needle 9 into the injection site. A feedback may be provided to the user to indicate that dispensing of the medicament is being initiated. For example, a tactile feedback may be provided in the form of an increased resistance as the container spring 13 compresses.

Figure 5:
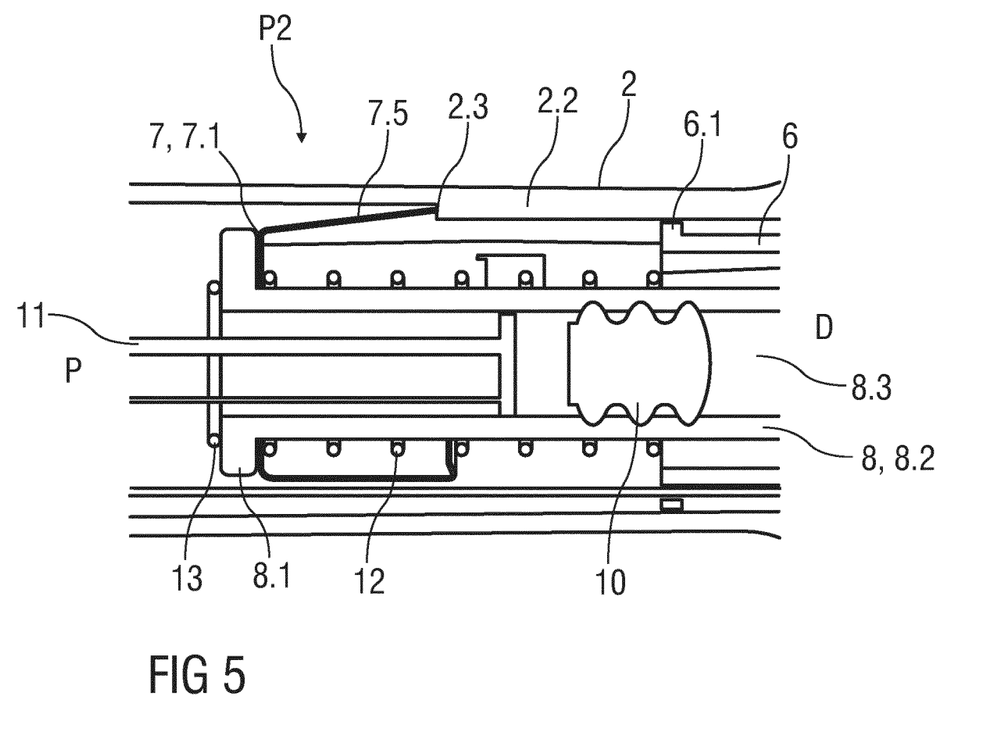
FIG. 5 is a schematic longitudinal detail section of an exemplary embodiment of a medicament delivery device during use.
Figure 7:
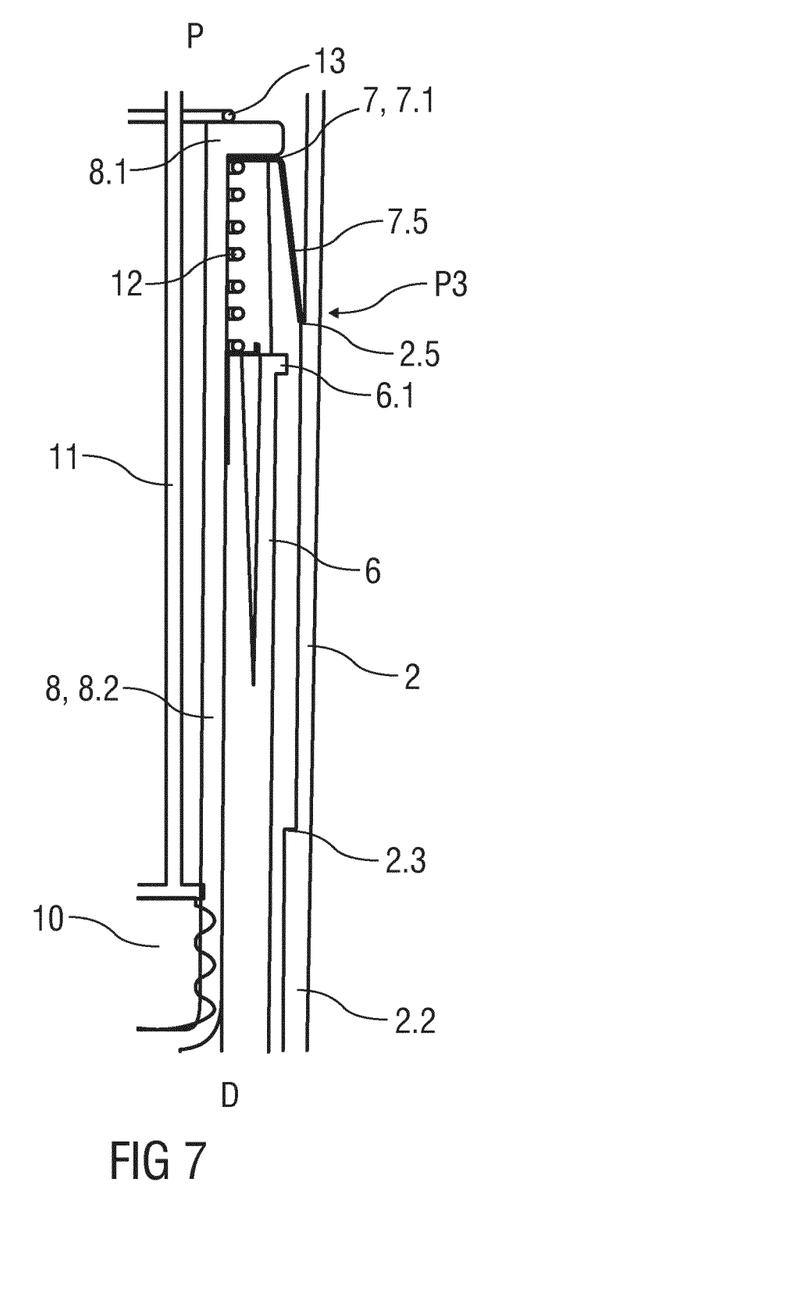
FIG. 7 is a longitudinal detail section of an exemplary embodiment of a medicament delivery device during use.

As shown in FIGS. 5 and 7, as the carrier 7 and the syringe 8 move proximally relative to the body 2, the second legs 7.5 are radially outwardly abutted by one or more first ribs 2.2. When the carrier 7 has traveled a sufficient proximal distance relative to the body 2, the second legs 7.5 deflect radially outward and may abut a second axial stop 2.3 on a proximal end of the first rib 2.2. Due to the second axial stop 2.3, the carrier 7 is prevented from moving in the distal direction D relative to the body 2. A third axial stop 2.5 may be disposed in the body 2 proximal of the second axial stop 2.3. When the second legs 7.5 proximally pass the third axial stop 2.5, the second legs 7.5 may deflect radially outward to abut the third axial stop 2.5 and prevent the carrier 7 from moving distally relative to the body 2. Those of skill in the art will understand that any number of axial stops may be formed in the body 2. Further, the axial stop may be formed as a rib with a transverse abutment surface or as a ramped surface with a transverse abutment surface. In an exemplary embodiment, a feedback (e.g., tactile and/or audible) may be provided when the carrier 7 proximally passes an axial stop. For example, when the second legs 7.5 deflect radially outward after proximally passing an axial stop, the second legs 7.5 may impact the body 2 generating a tactile feedback (e.g., a vibration) and/or an audible feedback (e.g., a 'click' sound). If the medicament delivery device 1 is removed from the injection site, the carrier 7 would travel in the distal direction D relative to the body 2 until the second legs 7.5 engage an axial stop, and the sleeve 6 would travel distally relative to the carrier 7 until the collar 6.1 abuts the first protrusion 7.3. Thus, the needle 9 would be covered again by the sleeve 6 despite the changed axial position of the carrier 7 and the syringe 8 relative to the body 2.

Figure 6:
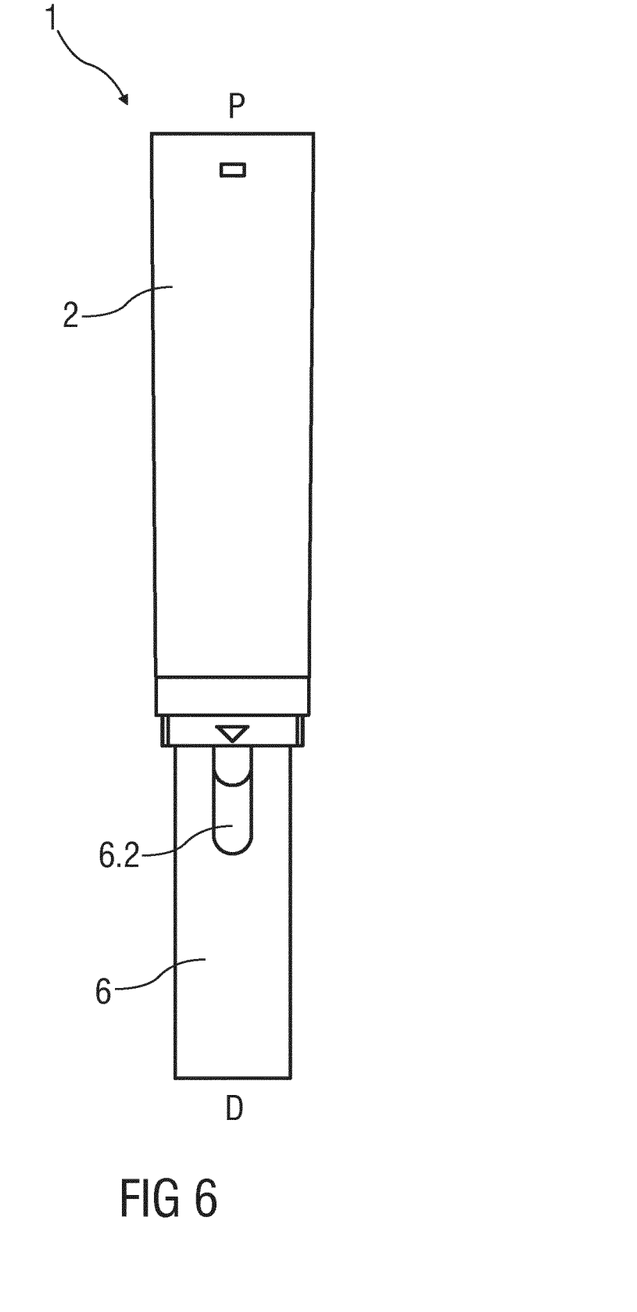
FIG. 6 is a schematic longitudinal section of an exemplary embodiment of a medicament delivery device during use.

FIG. 6 is a schematic view of the medicament delivery device 1 during use. An overall length of the medicament delivery device 1 is shorter than in an initial state, and the sleeve window 6.2 is partially hidden within the body 2 thus providing a visual indication that the medicament delivery device 1 has been used. If the medicament delivery device 1 is in this state, it can be re-applied against the injection site (or a different injection site) and the medicament delivery. For example, a dose of a medicament may need to be administered in at two different injection sites. Thus, the medicament delivery device 1 could be used to administer a first partial dose at a first injection site. A feedback provided by the second legs 7.5 and an axial stop may indicate that the first partial dose is complete. The medicament delivery device 1 could then be relocated (with the distal tip of the needle 9 covered by the sleeve 6) to a second injection site to deliver a second partial dose. Due to the sleeve spring 12 being weaker than the container spring 13, the sleeve 6 will again move relative to the carrier 7 thus inserting the needle 9 into the injection site before the syringe 8 and carrier 7 move relative to the body 2 for delivering the medicament.

Figure 8:
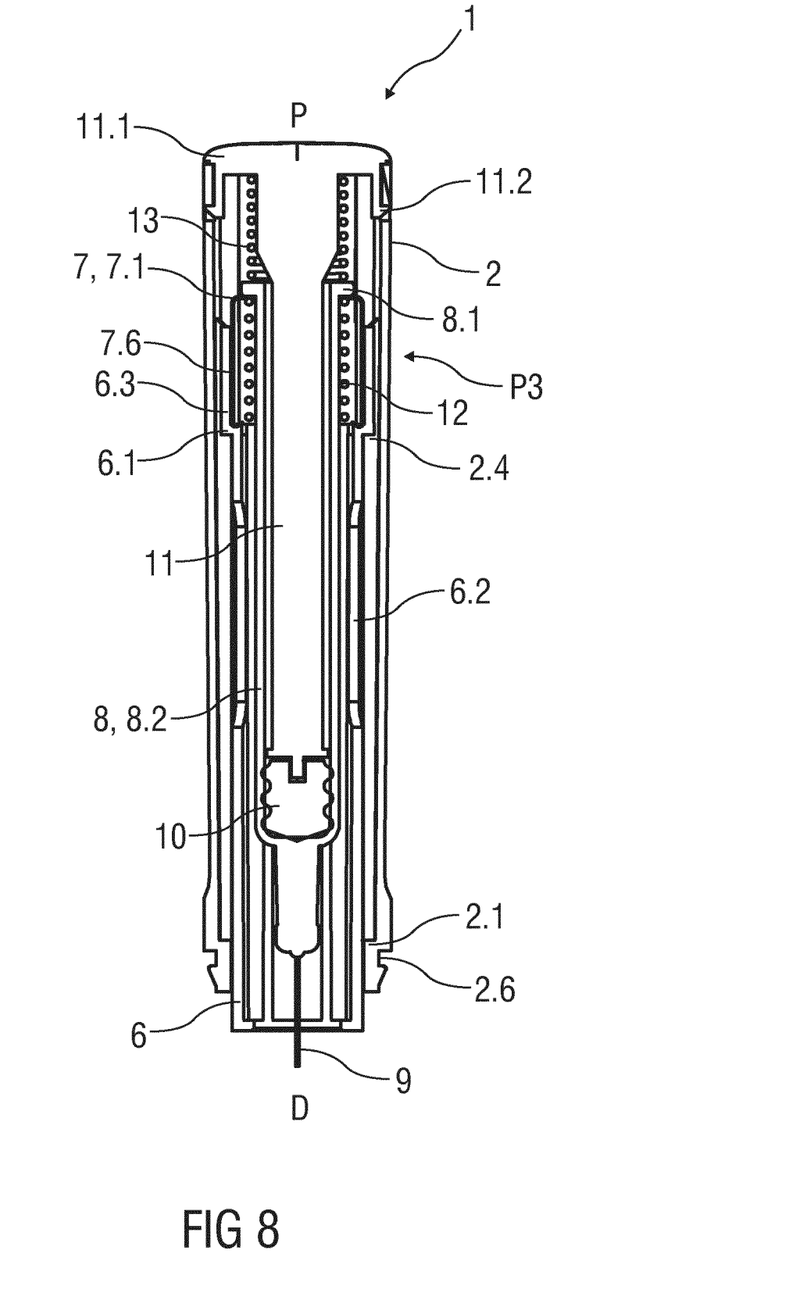
FIG. 8 is a schematic longitudinal section of an exemplary embodiment of a medicament delivery device during use.

As shown in FIG. 8, as the body 2 is pressed further against the injection site, the piston rod 11 will displace the stopper 10 until the stopper 10 bottoms out within the syringe 8 (or delivers the intended dose). At this point the force opposing the movement of the body 2 in the distal direction D relative to the sleeve 6 considerably increases providing a tactile feedback to indicate that the injection is finished. The second legs 7.5 may engage an axial stop (e.g., third axial stop 2.5) to prevent the carrier 7 from moving distally relative to the body 2.

Figure 9:
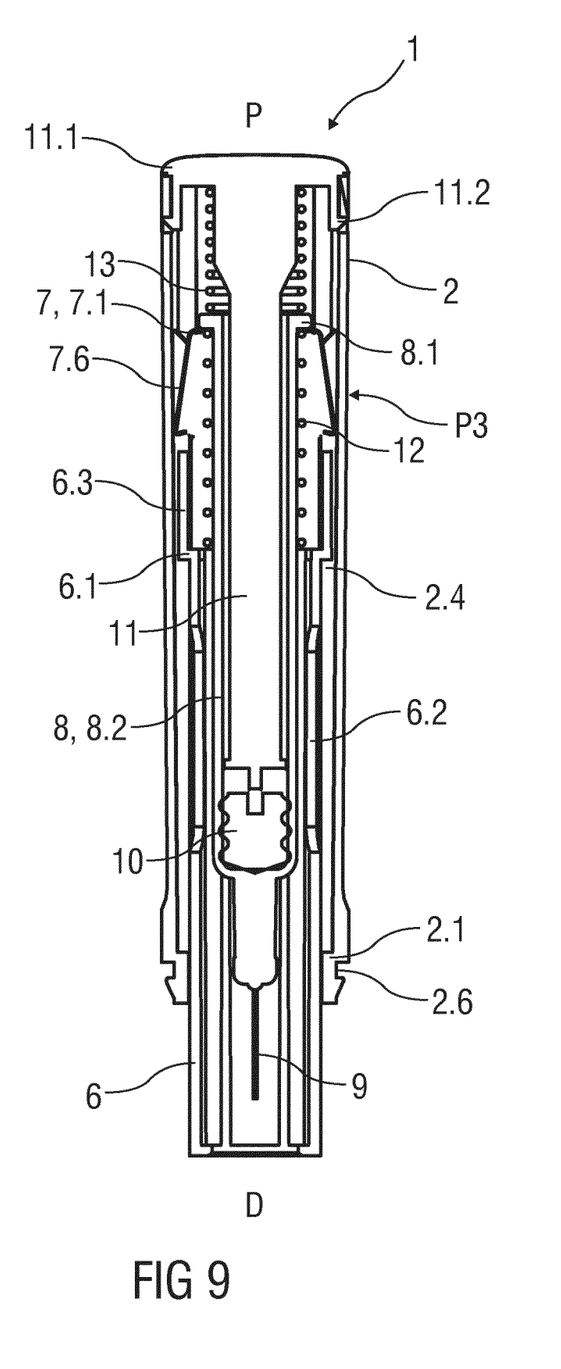
FIG. 9 is a schematic longitudinal section of an exemplary embodiment of a medicament delivery device after use.

As shown in FIG. 9, when the medicament delivery device 1 is removed from the injection site, the sleeve spring 12 returns the sleeve 6 in the distal direction D relative to the carrier 7 until the collar 6.1 abuts the first protrusion 7.3. As the sleeve 6 translates distally, the sleeve legs 6.3 disengage the third legs 7.6 of the carrier 7 allowing them to radially outwardly deflect. Due to the movement of the sleeve 6 relative to the carrier 7 the distal tip of the needle 9 is covered again by the sleeve 6. On an attempt to again move the sleeve 6 in the proximal direction P relative to the body 2, the sleeve legs 6.3 axially abut the outwardly deflected third legs 7.6 preventing re-exposure of the needle 9. The length of the second rib 2.4 can be modified in order to adapt the position and hence the percentage of medicament delivered at which the third legs 7.6 are allowed to deflect radially outwards and lock out the sleeve 6.

In an exemplary embodiment, the cap 3 of the medicament delivery device 1 serves for keeping the needle 9 sterile prior to use, for removing the protective needle shield 14, for preventing unintended use of the medicament delivery device 1 prior to removal of the cap 3 and for providing rigid packaging.

In an exemplary embodiment, the medicament delivery device 1 allows for application by a user, e.g. a patient or caregiver, wherein the body 2 can be held in one hand. The needle 9 of the medicament delivery device 1 is hidden from view during all states of operation.

In an exemplary embodiment, the insertion depth of the needle 9 is defined by the initial distance of the distal tip of the needle 9 from the distal end of the sleeve 6 and by the distance between the first protrusion 7.3 and the second protrusion 7.4 on the carrier 7 limiting relative axial movement of the sleeve 6.

In an exemplary embodiment, the forces required to insert the needle 9 into the injection site and to deliver the medicament can be adjusted by respectively selecting the sleeve spring 12 and the container spring 13, wherein the force for delivering the medicament depends on the container spring 13 and on the characteristics of the syringe 8, stopper 10, needle 9 and medicament.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39),
wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2,
H-Asn-(Glu)5-des Pro36, Pro37, Pro38 [Met(O)14, Trp (O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by A and K. A light chain has two successive domains: one constant domain (CL) and one variable domain (VL). The approximate length of a light chain is 211 to 217 amino acids. Each antibody contains two light chains that are always identical; only one type of light chain, K or A, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. A medicament delivery device comprising:
   a body;
   a container carrier slidably disposed in the body and configured to retain a medicament container, the container carrier comprising at least two legs biased radially outward; and
   a sleeve slidably coupled to the container carrier and configured to cover a needle, wherein:
   the body comprises at least one axial stop adapted to axially abut a second leg of the at least two legs;
   the sleeve includes at least one sleeve leg adapted to radially abut a third leg of the at least two legs when the sleeve is in a retracted position relative to the body; and
   the third leg is adapted to axially abut the at least one sleeve leg to lock the sleeve in an extended position relative to the body.

2. The medicament delivery device according to claim 1, wherein the at least two legs include a first leg having a first protrusion and a second protrusion proximal of the first protrusion.

3. The medicament delivery device according to claim 2, wherein the sleeve includes a collar adapted to abut the first protrusion and the second protrusion.

4. The medicament delivery device according to claim 2 wherein:
   at least one of the first leg, the second leg and the third leg is coupled to a periphery of a proximal portion of the container carrier; and
   at least one of the first leg, the second leg and the third leg extends in a distal direction from the proximal portion.

5. The medicament delivery device according to claim 4, wherein the proximal portion of the container carrier is adapted to receive the container.

6. The medicament delivery device according to claim 1, further comprising a plunger rod disposed within the body.

7. The medicament delivery device according to claim 6, wherein the plunger rod is fixed to the body.

8. The medicament delivery device according to claim 1, further comprising a sleeve spring biasing the sleeve relative to the container carrier.

9. The medicament delivery device according to claim 8, wherein the sleeve spring biases the sleeve toward the first protrusion.

10. The medicament delivery device according to claim 1, further comprising a container spring biasing the carrier relative to the body.

11. The medicament delivery device according to claim 1 wherein the sleeve includes one or more sleeve windows.

12. The medicament delivery device according to claim 1, further comprising a cap removably coupled to the body.

13. The medicament delivery device according to claim 12, wherein the cap includes a viewing window.

14. The medicament delivery device according to claim 12, wherein the cap includes one or more indicia indicating an intended orientation of the device.

15. The medicament delivery device according to claim 1, further comprising the container including a medicament.

16. The medicament delivery device according to claim 1, further comprising the container including a pharmaceutically active compound.

\* \* \* \* \*